(12) United States Patent
Cerceo

(10) Patent No.: US 7,998,476 B2
(45) Date of Patent: Aug. 16, 2011

(54) **METHOD OF TREATMENT USING *ASPERGILLUS ORYZAE* PROTEASE**

(75) Inventor: Joseph Cerceo, Elkton, MD (US)

(73) Assignee: Standard Biologics, Inc., Elkton, MD (US)

( * ) Notice: Subject to any disclaimer, the term of this patent is extended or adjusted under 35 U.S.C. 154(b) by 0 days.

(21) Appl. No.: 11/941,399

(22) Filed: Nov. 16, 2007

(65) Prior Publication Data

US 2008/0118492 A1 May 22, 2008

Related U.S. Application Data

(60) Provisional application No. 60/860,482, filed on Nov. 22, 2006.

(51) Int. Cl.
*A61K 38/48* (2006.01)

(52) U.S. Cl. ..................... 424/94.63; 435/225

(58) Field of Classification Search ............. None
See application file for complete search history.

(56) References Cited

U.S. PATENT DOCUMENTS

| | | | |
|---|---|---|---|
| 3,905,869 A | 9/1975 | Hidaka et al. | |
| 3,932,618 A | 1/1976 | Fujii et al. | |
| 3,940,478 A | 2/1976 | Kurtz | |
| 4,844,897 A | 7/1989 | Maeda et al. | |
| 5,500,359 A | 3/1996 | Boyer et al. | |
| 5,560,910 A | 10/1996 | Crandall | |
| 5,560,914 A | 10/1996 | Ghoneum et al. | |
| 5,562,900 A | 10/1996 | Boyer et al. | |
| 5,662,902 A | 9/1997 | Boyer et al. | |
| 5,662,903 A | 9/1997 | Boyer et al. | |
| 6,361,800 B1 | 3/2002 | Cooper et al. | |
| 6,413,512 B1* | 7/2002 | Houston et al. | 424/94.63 |
| 6,953,588 B2 | 10/2005 | Cooper et al. | |
| 7,067,124 B2 | 6/2006 | Davidson et al. | |
| 2003/0095961 A1 | 5/2003 | Houston et al. | |
| 2004/0057944 A1 | 3/2004 | Galle et al. | |
| 2004/0191237 A1 | 9/2004 | Davidson et al. | |
| 2005/0214383 A1 | 9/2005 | Bubnis et al. | |
| 2005/0244510 A1* | 11/2005 | Smith | 424/617 |
| 2006/0216361 A1 | 9/2006 | Edwards et al. | |

FOREIGN PATENT DOCUMENTS

| | | |
|---|---|---|
| GB | 1 293 227 | 10/1972 |
| GB | 1 390 542 | 4/1975 |
| WO | WO 94/25580 A1 | 11/1994 |
| WO | WO 95/08998 A1 | 6/1995 |
| WO | WO 02/060474 A2 | 8/2002 |

OTHER PUBLICATIONS

Sarzi-Puttini et al., Seminars in Arthritis and Rheumatism, 2005, vol. 35 (Suppl), p. 1-10.*
Protease A-DS, Enzyme Material Safety Data Sheet, AMANO Enzyme Inc., Issue date Jan. 3, 2003.*
Wierik et al., International Journal of Pharmaceutics, 1996, vol. 134, p. 27-36.*
"Digestive Disorders," as presented by LifeExtension <www.lef.org> updated Jun. 5, 2003, accessed on Jul. 9, 2008.
"Dr. Gonzalez, Individualized Nutritional Protocols," as presented by Dr.Gonzalez.com <www.dr-gonzalez.com> accessed Jul. 15, 2008.
"Enzymes Derived from *Aspergillus oryzae*," as presented by IPCS Inchem <www.inchem.org> accessed Jul. 11, 2008.
"Enzymes in use for dietary purposes in the U.S. prior to Oct. 1994," as presented by the Enzyme Technical Association <www.enzymetechnicalassoc.org> last revised Jan. 1999, accessed Jul. 11, 2008.
"Enzymes to Improve Immune system Health-Protease and Cancer" as presented by HealthyNewAge <www.healthynewage.com> accessed Jul. 15, 2008.
"Expert Interview: Antiangiogenesis for Colorectal Cancer—an Evolving Therapeutic Strategy: An Expert Interview With Dr. Herbert Hurwitz," as presented by *Medscape Medical News* <www.medscape.com> released Jun. 21, 2006, accessed Jul. 9, 2008.
"Holistic Health Information—Enzymes, Herbs and Prostate Cancer," as presented by HealthyNewAge <www.healthynewage.com> accessed Jul. 15, 2008.
"N.D.M., Nutrition, L.L.C.," <www.ndmnutrition.com> accessed Jul. 15, 2008.
"Nutritional Therapeutics Division of Standard Biologics, Inc.™," <nutritionaltherapeutics.com> accessed Jul. 15, 2008.
"Protease," as presented by Greenwood Health Systems <www.greenwoodhealth.net> accessed Jul. 10, 2006.
"The Healing Power of Proteolytic Enzymes," Dr. Murray, Natural Living, as presented by DoctorMurray.com <www.doctormurray.com> accessed Jul. 15, 2008.
"The Science of ProZime-440™," as presented by ProVision Naturals™ <www.provisionnaturals.com> accessed Jul. 11, 2008.
Ackerson, A., et al., "Nutritional Support of Osteoporosis," as presented by HealingYou <www.healingyou.org> accessed Jul. 11, 2008.

(Continued)

*Primary Examiner* — Kade Ariani
(74) *Attorney, Agent, or Firm* — Nevrivy Patent Law Group P.L.L.C.

(57) ABSTRACT

A method for treating various diseases, conditions and injuries with a protease preparation derived from *Aspergillus oryzae* and made using potato dextrin as the carbohydrate source is described. The method comprises orally administering the *Aspergillus oryzae* protease preparation on an empty stomach and in an amount greater than about 2,000,000 HUT per day. Additionally, a method for treating various diseases, conditions and injuries with a protease derived from *Aspergillus oryzae* made using potato dextrin as the carbohydrate source along with a nutritional supplement of vitamins and minerals is also described. The method comprises orally administering the *Aspergillus oryzae* protease preparation on an empty stomach in an amount of greater than 2,000,000 HUT per day and administering the dietary supplement of vitamins and minerals orally with food.

19 Claims, No Drawings

OTHER PUBLICATIONS

Amano Enzyme product List Copyright © 2007.

Andersen, G.D., "Proteolytic Enzymes—Part III," *Dynamic Chiropractic 9*, as presented by Chiroweb <www.chiroweb.com> accessed Jul. 11, 2008.

Aprahamian, M., et al., "Efficiency of pantothenic acid on wound healing: effect of an increase of iron and copper content of the tissues," *Eur. Surg. Res. 15*:61, Abstract No. 96, Karger (1983).

Banford, J.C., et al., "Serum copper and erythrocyte superoxide dismutase in rheumatoid arthritis," *Ann. Rheum. Dis. 41*:458-462, BMJ Publishing Group (1982).

Barclay, L., "Older Adults May Need B12 Dose More Than 200 times the RDA to Normalize Mild Vitamin Deficiency," as presented by *Medscape Medical News* <www.medscape.com> released May 27, 2005, accessed Jul. 14, 2008.

Barton-Wright, E.C and Elliot, W.A., "The Pantothenic Acid Metabolism of Rheumatoid Arthritis,," *Lancet 2*:862-863, Lancet Publishing Group (1963).

Berdanier, C.D., "Integration of the Functional Aspects of Vitamins and Minerals," in *Advanced Nutrition Micronutrients*, Unit 2, CRC Press LLC, Boca Raton, Florida, pp. 9-20 (1998).

Berger, B., et al., "Useful hydrolytic enzymes: Proteases, lipases and nitrilases," *Pure & Appl. Chem. 64*:1085-1088, International Union of Pure and Applied Chemistry (1992).

Bergkvist, R., "The Proteolytic Enzymes of *Aspergillus oryzae*, II: Properties of the Proteolytic Enzymes," *Acta. Chem. Scand. 17*:1541-1551, Munksgaard International Publishers (1963).

Biesebeke, R., et al., "Branching mutants of *Aspergillus oryzae* with improved amylase and protease production on solid substrates," *Appl. Microbiol. Biotechnol. 69*:44-50, Springer Verlag (Nov. 2005).

Bitomsky, M., "Digestive Enzymes: the Missing Link," *LE Magazine*, Life Extension Foundation (1999).

Black Hills Health Products, Inc. information on enzyme supplements as presented by NDMnutrition <www.ndmnutrition.com> accessed Jul. 2, 2006.

Brouillette, K.M., ed., "Chapter 13: The Musculoskeletal System," in *Athletic Training and Sports Medicine*, American Academy of Orthopaedic Surgeons, Park Ridge, IL, pp. 192-202 (1991).

Combs, G.F., "Chapter 6: Vitamin D," in *The Vitamins: Fundamental Aspects in Nutrition and Health*, Academic Press, San Diego, CA, pp. 151-178 (1992).

Crewther, W.G. and Lennox, F.G., "Enzymes of *Aspergillus oryzae*. IV. Fractionation and Preparation of Crystals Rich in Protease," *Aust. J. Sci. Res. 6*:429-446, Commonwealth Scientific and Industrial Research Organization (1953).

Crewther, W.G. and Lennox, F.G., "Preparation of Crystals Containing Protease from *Aspergillus oryzae*," *Nature 165*:680, Nature Publishing Group (1950).

Diffang, C. and Saldeen, T., "Effect of Brinase (Protease I from *Aspergillus oryzae*) on the Elimination of Fibrin from the Lungs and Pulmonary Damage in Rats with Induced Intravascular Coagulation and Inhibited Fibrinolysis," *Thromb. Res. 9*:611-622, Pergamon Press (1976).

Doi, Y., et al., "Substrate Specificities of Deuterolysin from *Aspergillus oryzae* and Electron Paramagnetic Resonance Measurement of Cobalt-substituted Deuterolysin," *Biosci. Biotechnol. Biochem. 67*:264-270, Japan Society for Bioscience, Biotechnology, and Agrochemistry (2003).

Donoho, C.R., and Rylandee, C.R., "Proteolytic Enzymes in Athletic Injuries a Double-Blind Study of a New Anti-Inflammatory Agent," *Del. Med. J. 34*:168-170, Medical Society of Delaware (1962).

Dryburgh, D.R., "Vitamin C and Chiropractic," *J. Manip. Physiol. Ther. 8*:95-103, National University of Health Sciences (1985).

Dunham, J., "Chapter 1: Metabolism of the Fracture Callus," in *Bone*, vol. 5: *Fracture Repair and Regeneration*, Hall, B., ed., CRC Press, Boca Raton, Florida, pp. 1-31 (1992).

Fenech, M., "Micronutrients and genomic stability: a new paradigm for recommended dietary allowances (RDAs)," *Food Chem. Toxicol. 40*:1113-1117, Elsevier Science (2002).

Fernando, R., et al., "Proteolytic Action of *Aspergillus niger* Extract on Influenza Virus," *Intervirology 14*:167-172, Karger (1980).

Final Report, in Collection of Information on Enzymes, Federal Enviornment Agency Austria and the Inter-University Research Center for Technology, Work and Culture, European Communities (2002).

Frisch, E.P., "Clinical Review on Brinase, a Protease from *Aspergillus oryzae*," *Folia Haematol. 101*:62-82, Akademische Verlagsgesellschaft M.B.H. (1974).

Gomi, K., et al., "Cloning and Nucleotide Sequence of the Acid Protease-encoding Gene (pepA) from *Aspergillus oryzae*," *Biosci. Biotech. Biochem. 57*:1095-1100, Japan Society for Bioscience, Biotechnology, and Agrochemistry (1993).

Grant, D. and Fisher, B., "Sports Injuries and Inflammation," as presented by Optimal Health Systems <www.optimalhealthsystems.com> accessed Jul. 11, 2008.

Havsteen, B., "Flavonoids, a Class of Natural Products of High Pharmacological Potency," *Biochem. Pharmacol. 32*:1141-1148, Pergamon Press (1983).

Ichishima, E., "Unique Catalytic and Molecular Properties of Hydrolases from *Aspergillus* used in Japanese Bioindustries," *Biosci. Biotechnol. Biochem. 64*:675-688, Japan Society for Bioscience (2000).

Kagan, V.E., et al., "Chapter 9: The Significance of Vitamin E and Free Radicals in Physical Exercise," in *Nutrition in Exercise and Sport, $2^{nd}$ Edition*, Wolinsky, I. and Hickson, J., eds., CRC Press, Boca Raton, Florida, pp. 185-213 (1994).

Kellems, R.O., et al., "Effect of Feeding *Aspergillus oryzae* Fermentation Extract or *Aspergillus oryzae* plus Yeast Culture plus Mineral and Vitamin Supplement on Performance of Holstein Cows During a Complete Lactation," *J. Dairy Sci. 73*:2922-2928, American Dairy Science Association (1990).

Knight, C., "Immunogenic Properties of PR8 Influenza Virus after Treatment with Acid Protease," *Intervirology 14*:37-43, Karger (1980).

Kolodny, A., "Double-Blind Evaluation of Asperkinase, A New Proteolytic Enzyme," *Am. J. Orthop. 5*:234-235, Texas Orthopedic Association (1963).

Kushner, I., "The Phenomenon of the Acute Phase Response," *Ann. N.Y. Acad. Sci. 389*:39-48, The New York Academy of Sciences (1982).

Lee, B.R., et al., "Aorsin, a novel serine proteinase with trypsin-like specificity at acidic pH," *Biochem. J. 371*:541-548, Biochemical Society (2003).

Leipner, J. and Saller, R., "Systemic Enzyme Therapy in Oncology Effect and Mode of Action," *Drugs 59*:769-780, Adis International Limited (2000).

Loo, J.V., et al., "Functional food properties of non-digestible oligosaccharides: a consensus report from the ENDO project (DGXII AIRII-CT94-1095)," *Br. J. Nutri. 81*:121-132, Nurition Society (1999).

López-Fandiño, R., et al., "Proteolytic activity of two commercial proteinases from *Aspergillus oryzae* and *Bacillus subtilis* on ovine and bovine caseins," *J. Diary Res. 58*:461-467, Journal of Diary Research (1991).

Lund, F., et al., "Thrombolytic Treatment with I.V. Brinase of Advanced Arterial Obliterative Disease of the Limbs," *Angiology 26*:534-556, Angiology Research Foundation (1976).

Machida, M., et al., "Genome sequencing and analysis of *Aspergillus oryzae*," *Nature 438*:1157-1161, Nature Publishing Group (Dec. 2005).

Maxwell, M., "Enzymes of *Aspergillus oryzae*. I. The Development of a Culture Medium Yielding High Protease Activity," *Aust. J. Sci. Res. 5*:42-55, Commonwealth Scientific And Industrial Research Organization (1952).

Mizuno, S., et al., "Release of Short and Proline-Rich Antihypertensive Peptides from Casein Hydrolysate with an *Aspergillus oryzae* Protease," *J. Dairy Sci. 87*:3183-3188, American Dairy Science Association (2004).

Ogston, D. and Ogston, C.M., "In Vitro Studies on a Proteolytic Enzyme from *Aspergillus oryzae* (Protease I)," *Thromb. Diath. Haemorrh. 29*:136-144, F. K. Schattauer Verlag (1968).

Oshiba, S., et al., "Enzymatic and Physiological Studies on the Proteases Heterogenous to the Body," *Kobe J. Med. Sci. 9*:139-149, Kobe University School Of Medicine (1963).

Pennington, J.A.T., et al., "Mineral content of foods and total diets: The Selected Minerals in Food Survey," 1982 to 1984, *J. Am. Diet. Assoc. 86*:876-891, The American Diabetic Association (1986).

Quirin, H., "Pain and Vitamin B1 Therapy," *Biblthca. Nutr. Dieta 38*:110-111, Karger, Basel (1986).

Reeves, P.G., "Chapter 13: Copper" in *Sports Nutrition Vitamins and Trace Elements*, Wolinsky, I., and Driskell, J.A., eds., CRC Press, Boca Raton, Florida, pp. 175-187 (1997).

Roth, F.R., et al., "Proteolytic Action of *Aspergillus niger* Extract on Influenza Virus," *Intervirology 14*:167-172, American Association of Immunologists (1980).

Saadat, F., et al., "Inhibitory effect of *Aspergillus fumigatus* extract on *matrix metalloproteinases* expression," *Mycopathologia 158*:33-37, Kluwer Academic Publishers (2004).

Sano, J., et al., "Effect of Casein Hydrolysate, Prepared with Protease Derived from *Aspergillus oryzae*, on Subjects with High-Normal Blood Pressure or Mild Hypertension," *J. Med Food 8*:423-430, Mary Ann Liebert (Dec.-Mar. 2005).

Setnikar, I., et al., "Antiarthritic Effects of Glucosamine Sulfate Studied in Animal Models," *Arzneim.-Forsch. Drug Res. 41*:542-545, Verlag (1991).

Setnikar, L., et al., "Absorption, Distribution, and Excretion of Radioactivity after a Single Oral Administration of Glucosamine to the Rat," *Pharmatherapeutica 3*:538-550, Clayton-Wray Publications (1984).

Short, S.H., "Chapter 16: Surverys of Dietary Intake and Nutrition Knowledge of Athletes and Their Coaches," in *Nutrition in Exercise and Sport 2nd Edition*, Wolinsky, I., and Hickson, J.F., eds., CRC Press, Inc., Boca Raton, Florida, pp. 367-416 (1994).

Singh, S., et al., "Isolation, structure, and HIV-1-integrase inhibitory activity of structurally diverse fungal metabolites," *J. Ind. Microbiol. Biotechnol. 30*:721-731, Springer (2003).

Smyth, H., et al., "The effects of protease I of *Aspergillus oryzae* (brinase) on membrane permeability and growth of Landschütz ascites tumour cells," *Int. J. Cancer 7*:476-482, Wiley-Liss (1971).

Stoecker, B.J., "Chapter 34: Chromium" in *Present Knowledge in Nutrition*, 7th edition, Ziegler, E.E. and Filer, L.J., eds., ILSI Press, Washington D.C., pp. 344-352 (1996).

Strain, J.J., "A Reassessment of Diet and Osteoporosis Possible Role for Copper," *Med. Hypoth. 27*:333-338, Longman Group UK Ltd. (1988).

Supplement profile for Nightly Essense™, as presented by Youngevity <www.youngevity.com> accessed Jul. 11, 2008.

Supplement profile for PhytoBioForte Super as presented by Greenwood Health Systems <www.greenwoodhealth.net> accessed Jul. 10, 2006.

Supplement profile for PureZyme™ as presented by EnzymEssentials <www.enzymeessentials.com> accessed Jun. 29, 2006.

Supplement profile for Ultra Juice®, as presented by eVitamins <www.evitamins.com> accessed Jul. 11, 2008.

Supplement profile for VitalzymX™—Extra-Strength Inflammation Control, as presented by CostLess Vitamin <www.costlessvitamin.com> accessed Jul. 11, 2008.

Supplement profile for Zest for Life® Enzyme boost formula as presented by AnyVitamins <http://www.anyvitamins.com> accessed Jul. 11, 2008.

Šutiak, V., et al., "The Induction of Inflammation in Mouse Tails with *Aspergillus oryzae* Protease and the Inhibitory effects of Synthetic and Natural Substances In Vitro," *Acta Vet. Brno 52*:345-354, University School Of Veterinary Medicine (2002).

Tinker, D., and Rucker, R.B., "Role of Selected Nutrients in Synthesis, Accumulation, and Chemical Modification of Connective Tissue Proteins," *Physiol. Rev. 65*:607-657, American Physiological Society (1985).

Tsujita, Y., and Endo, A., "Presence and Partial Characterization of Internal Acid Protease of *Aspergillus oryzae*," *Appl. Enviorn. Microbiol. 36*:237-242, American Society of Microbiology (1978).

Vreugdenhil, G., et al., "Anaemia in rheumatoid arthritis: the role of iron, vitamin $B_{12}$, and folic acid deficiency, and erythropoietin responsiveness," *Ann. Rheum. Dis. 49*:93-98, BMJ (1990).

Wheatley, D., et al., "Calcium pantothenate in arthritic conditions," *Practitioner 224*:208-211, Morgan Grampion Publishers (1980).

Branch, R.W. (Exec. Prod.), *A Pet Story*, copyright 2000 (CD Provided). Made public in 2000 by Animal Planet®, Discovery Communications, LLC.

\* cited by examiner

METHOD OF TREATMENT USING *ASPERGILLUS ORYZAE* PROTEASE

BACKGROUND OF THE INVENTION

1. Field of the Invention

The present invention is directed to the use of an *Aspergillus oryzae* protease preparation as an anti-inflammatory agent useful in the treatment of various diseases and conditions.

2. Background of the Invention

Proteolytic enzymes have been used extensively as therapeutic agents for decades. The earliest studies used pancreatic enzymes in the treatment of cancer. Later, proteolytic enzymes from non-animal sources such as the plant enzymes bromelain and papain and proteases derived from fungi such as *Aspergillus* sp. were investigated.

Proteases from *Aspergillus oryzae* are commercially used in the production of sake and soy sauce as well as in flavoring of other food products. Clinically, these enzymes have been shown to have an anti-thrombolytic/anti-hypertensive effect (Frish, E., "Clinical Review on Brinase, a Protease from *Aspergillus oryzae*," *Folia Haematol.*, 101(1):63-82 (1974), Mizuno, S., et al., "Release of Short and Proline-Rich Hypertensive Peptides from Casein Hydrolysate with an *Aspergillus oryzae* Protease," *J. Dairy Sci.*, 87:3183-3188 (2004), Sano, J., et al., "Effect of Caesin Hydrolysate Prepared with Protease Derived from *Aspergillus oryzae*, on Subjects with High-Normal Blood Pressure or Mild Hypertension," *J. Medicinal Food*, 8(4):423-430 (2005)), anti-cancer effect (Smyth, H., et. al., "The Effects of Protease I of *Aspergillus oryzae* (Brinase) on Membrane Permeability and Growth of Landshutz Ascites Tumour Cells," *Int. J. Cancer*, 7:476-482 (1971), U.S. Pat. No. 5,562,900), and an anti-viral effect (Knight, C., "Immunogenic Properties of PR9 Influenza Virus After Treatment with Acid Protease," *Intervirology*, 14:37-43(1980), Roth, R., et al., "Proteolytic Action of *Aspergillus niger* Extract on Influenza Virus," *Intervirology*, 14:167-172 (1980), Singh, S., et al. "Isolation, Structure, and HIV-1 Integrase Inhibitory Activity of Structurally Diverse Fungal Metabolites," *J. Ind. Microbiol. Biotechnol.*, 30:721-731 (2003)). In addition, proteases from *Aspergillus oryzae* have been shown to be potent anti-inflammatory mediators (Kolodny, A., "Double Blind Evaluation of Asperkinase, a New Proteolytic Enzyme," *Am. J. Orthopedics*, 234-235 (1963), U.S. Pat. No. 6,413,512 B1, U.S. Pat. No. 3,932,618, EP 1390 542).

In many diseases and injuries there is a marked increase in circulating proinflammatory cytokine levels. This increase in cytokine expression is hypothesized to contribute to the pathology of these conditions. Infection, cancer and tissue injury can all trigger the production of cytokines, which can then enter the blood stream to alter the physiology of distant tissues, or act locally as paracrine mediators. In some diseases and injury states cytokines are beneficial to the host, but in others, cytokines are detrimental to the host. Proteases and cytokines are intimately interrelated in that cytokines are involved in regulating the production of proteases and proteases are frequently involved in the liberation of soluble cytokines, as well as in their destruction. Diseases in which cytokines play a pathological role include multiple sclerosis, type I diabetes, rheumatoid arthritis, soft tissue injury, and solid tumor malignancies. It would be beneficial therefore in these disease states to decrease the levels of circulating cytokines. This has been accomplished by treating patients with antibodies to specific cytokines, i.e. TNFα, soluble receptor antagonists, and also proteases from plant and microbial sources.

Cytokines play a major role in the manifestation of inflammation, which is a predominant biological reaction to a myriad of injurious agents and events. It is well-known that host defensive and reparative processes in inflammation can be harmful to the body's welfare. Common characteristics of inflammation are fever, swelling, bruising and pain. The body's defensive mechanisms can bring about the release of products toxic to the host or lead to destruction of its host tissues.

Detrimental consequences of inflammation include fibrin deposition, and reduction in vascularity causing changes in tissue permeability creating additional morphologic barriers to the penetration of antibodies or pharmacological agents into the injured area. Some of the autolysis products released by tissue necrosis often constitute a good medium for microorganisms and can even antagonize the antimicrobial activity of many pharmaceutical agents, thereby exacerbating the injury or infection and prolonging the recovery process.

Cytokines released in the immune response to tumor antigens, such as IL-1β and IL-6 can upregulate angiogenic factors such as vascular endothelial growth factor (VEGF) which leads to new blood vessel formation providing nutrition to the growing malignancy, thereby helping the tumor to grow.

In addition, cytokines are pathogenic mediators in many autoimmune conditions such as rheumatoid arthritis (RA), multiple sclerosis (MS) and Crohn's disease. Current treatments in RA focus on inhibiting tumor necrosis factor alpha (TNF-α) production and signaling. In animal models of MS, inhibition of interferon-γ has shown promise.

The absorption of orally-administered proteases in mammals has been extensively studied. The prevailing finding of these studies is that proteases can be partially absorbed intact, with activity preserved, from the digestive tract and subsequently distributed systemically in the blood. Proteolytic enzymes from *Aspergillus oryzae* are often used as digestive aids, and as such stimulate bowel movements, often times leading to diarrhea in the host.

Early in the study of proteases, it was observed that the administration of animal-derived proteases could accelerate the healing of inflamed sites. Therefore, a large database exists of clinical results from orally-administered, animal derived proteases establishing the effectiveness of these proteases as therapeutic agents for inflammatory conditions. However, a clear mechanism of physiological action for animal-derived proteases is yet to be determined. Plant proteases have also been found to have a positive effect on inflammation The largest body of evidence supporting the use of proteases for inflammatory conditions studied the effects of a mixture of papain, bromelain, trypsin, chymotrypsin, pancreatin and rutin. In most cases, the mixture was in addition to standard medical care.

It has long been established that a number of chemical compounds typically referred to as vitamins and minerals provide significant health value and treat specific medical conditions, particularly when supplied in therapeutic doses. Over the years, a number of such vitamins and minerals have been identified. For example, vitamins include A, C, D, E, and the family of B vitamins and minerals include iron, zinc, calcium and chromium. The human body does not synthesize most of these vitamins and minerals which are essential to maintaining the health of the human body. Thus these necessary vitamins and minerals must be obtained from an external source. The two most common external sources are foods and nutritional supplements. Food is typically the primary source of obtaining the necessary nutrients for maintaining health, however many people do not eat foods that consistently provide the necessary daily requirements of vitamins and minerals. Thus, vitamin and mineral nutritional supplementation has become a recognized method of meeting these daily requirements.

While certain vitamins and minerals have been shown to be essential for the maintenance an individual's health, the use of vitamin and mineral nutritional supplementation has afforded the possibility to include micro-nutrients which, although not absolutely essential to maintaining health, provide significant benefit toward maintaining health.

U.S. Pat. No. 6,413,512 B1 describes treating patients suffering from a disease resulting from increased cytokine production with a pharmaceutical composition comprising 2 or more proteases from a microbial source in an amount of between 20,000 HUT and 550,000 HUT. The protease described this patent is made using rice and/or wheat bran as the carbohydrate source.

In light of the above, the present invention is based on the surprising result that proteases from *Aspergillus oryzae* made using potato dextrin as the carbohydrate source are better absorbed by the proximal small intestine than proteases using rice or wheat bran as the carbohydrate source and thus are exceptionally potent anti-inflammatory mediators. Proteases made using potato dextrin as the carbohydrate source, in contrast to those made from rice and or wheat bran, reduce gastrointestinal side effects such as diarrhea. In addition, administering more than 2,000,000 HUT/day of *Aspergillus oryzae* protease made from potato dextrin, along with a specific multi-vitamin formulation, provides an optimal and therapeutic anti-inflammatory effect.

BRIEF SUMMARY OF THE INVENTION

The present invention provides a method of treating mammalian diseases and conditions by administering a protease preparation derived from *Aspergillus oryzae* made using potato dextrin as the carbohydrate source in an amount of more than about 2,000,000 HUT per day. The protease preparation is preferably given on an empty stomach four times daily. The mammalian disease treated by the method of the instant invention is preferably selected from the group consisting of rheumatoid arthritis, multiple sclerosis, Crohn's disease, viral infection, soft tissue injury, bacterial infection, solid tumor malignancy, osteoporosis, osteopenia, chronic obstructive pulmonary disease, and Alzheimer's disease.

Another embodiment of the invention provides a method of treating mammalian disease by adminstering a protease preparation derived from *Aspergillus oryzae* made using potato dextrin as the carbohydrate source at an amount of more than about 2,000,000 HUT per day, together with a nutritional supplement of vitamins and minerals. The nutritional supplement preferably contains vitamin A, vitamin B1, vitamin B2, vitamin B5, vitamin B6, vitamin B12, vitamin C, magnesium citrate, vitamin E, Vitamin D3, zinc citrate, manganese gluconate, copper gluconate, biotin, folate, chromium polynicotinate, citrus bioflavinoids, glucosamine sulfate, and boron sulfate. In the preferred embodiment, the dietary supplement is given 2-3 times per day with food while the protease preparation is given 4 times daily on an empty stomach.

In another embodiment an additional supplement of calcium is given. In the preferred embodiment calcium is given at a dose of 900 mg/day. It is preferred that the additional calcium supplement is given once daily in the evening.

DETAILED DESCRIPTION OF THE INVENTION

It is to be understood that this invention is not limited to the particular methods, compositions and materials disclosed herein as such methods, compositions and materials may vary. It is also understood that the terminology employed herein is used for the purpose of describing particular embodiments only and is not intended to be limiting since the scope of the present invention will be limited only by the appended claims and equivalents thereof.

It must also be noted that, as used in this specification and the appended claims, the singular forms "a," "an," and "the" include plural referents unless the context clearly dictates otherwise. Thus, for example, reference to "a protease" includes references to two or more of such proteases and "a vitamin" includes reference to one or more of such vitamins, unless otherwise specified.

In general the present invention is directed to a method of alleviating the manifestations of mammalian inflammatory disease or injury. The method of the present invention may be used to treat any type of inflammatory disease wherein pro-inflammatory cytokines are produced and exacerbate disease. Diseases that may be treated by the current invention include without limitation, rheumatoid arthritis, multiple sclerosis, Crohn's disease, viral infection, soft tissue injury, bacterial infection, solid tumor malignancy, osteoporosis, osteopenia, chronic obstructive pulmonary disease, and Alzheimer's disease.

The present invention offers improvements over prior proteolytic products in that, unlike other protease compositions, the primary benefit is obtained from the use of a protease from a particular microbial source in a defined dosing regimen. The invention does not contain animal-derived products, and thus is acceptable to patients who may object to the ingestion of animal products. The invention focuses specifically on protease preparations prepared using potato dextrin as the carbohydrate source instead of maltodextrin, wheat or rice bran. Surprisingly, protease preparations prepared using potato dextrin are more readily absorbed by the proximal small intestine and lead to less undesirable gastrointestinal side effects than those prepared with maltodextrin, wheat or rice bran. In addition, the invention does not contain gluten and may be safely ingested by persons who have an allergy to wheat gluten.

The preferred dietary supplement of the current invention comprises vitamin A, vitamin B1, vitamin B2, vitamin B5, vitamin B6, vitamin B12, vitamin C, magnesium citrate, vitamin E, vitamin D3, zinc citrate, manganese gluconate, copper gluconate, biotin, folate, chromium polynicotinate, citrus bioflavinoids, glucosamine sulfate, and boron sulfate.

The preferred dietary supplement comprises vitamin A. Vitamin A functions as a regulatory hormone with effects on specific genes for differentiation and maintenance of epithelial tissue, and is important to reproduction, vision and immune function. Taken in excess vitamin A will cause birth defects, and in the active or athletically performing individual, can cause bone demineralization, loss of elasticity in connective tissue, muscle soreness and joint pain. The recommended daily allowance (RDA) for vitamin A is 5000 IU/day. In the preferred embodiment of the invention the dietary supplement contains 5000 IU/day of vitamin A in the form of retinyl palmitate.

The preferred dietary supplement comprises vitamin B1. Vitamin B1 is distributed widely in foods in low concentrations. Vitamin B1 is susceptible to destruction by refining processes, neutral and alkaline conditions, heat and oxidation. Vitamin B1 is important in energy production from food, especially carbohydrates, and plays a vital role in nerve function. Supplementation in large doses is safe and has shown some efficacy in the ability to control pain in connective tissue. The RDA for vitamin B1 is 1.5 mg/day. In the preferred embodiment the dietary supplement contains 100 mg/day in the form of thiamin mononitrate.

The preferred dietary supplement comprises vitamin B2. Vitamin B2 is essential to a large number of redox reactions, releasing energy from carbohydrates, fats and amino acids, and is thus important to the elderly, and the active or athletic individual. Vitamin B2 is highly water soluble and reactive to light. Strict vegetarians, pregnant and lactating women, and ill or trauma victims are also at risk for vitamin B2 deficiency. High oral doses of vitamin B2 are essentially non-toxic. The RDA for vitamin B2 is 1-1.5 mg/day. In the preferred embodiment the dietary supplement contains 50 mg/day vitamin B2.

The preferred dietary supplement comprises vitamin B3 (niacinamide, not niacin). Vitamin B3 plays an important role in energy production, cellular respiration, fat synthesis and joint pain and mobility. Vitamin B3 (niacinamide, not niacin) possesses no known side effects, and when supplemented several times during the day, demonstrates long-lasting objective improvements in joint mobility. The RDA for vitamin B3 (niacin) is 15-20 mg/day. In the preferred embodiment the dietary supplement contains 300 mg/day vitamin B3 (niacinamide).

The preferred dietary supplement comprises vitamin B5. Vitamin B5 plays a significant role in energy production from carbohydrates, fats and proteins. The toxicity of vitamin B5 is negligible. Active and elderly individuals in trauma or who suffer from rheumatoid arthritis have realized significant improvements in morning stiffness, disability and pain when supplemented with gram doses of vitamin B5. There is no RDA for vitamin B5, a provisional range of intake of 4-87 mg/day was established 1980. In the preferred embodiment the dietary supplement contains 1000 mg/day vitamin B5 in the form of panthothenic acid.

The preferred dietary supplement comprises vitamin B6. Vitamin B6 has recently been shown to be vital to bone health. However in high doses, vitamin B6 can be toxic. In low doses, vitamin B6 shows no efficacy. Pregnant and lactating women, oral contraceptive users and heavy drinkers are at risk for vitamin B6 deficiency. The RDA for vitamin B6 is 1.5-2 mg/day. In the preferred embodiment the dietary supplement contains 50 mg/day vitamin B6 in the form of pyridoxine hydrochloride.

The preferred dietary supplement comprises vitamin B12. Vitamin B12 deficiencies can interfere with normal cell division involving arrested synthesis of DNA causing cellular mutations leading to disease states, particularly in bone marrow and intestinal mucosa. Vitamin B12 has no appreciable toxicity, and is frequently deficient in strict vegetarians. The RDA for vitamin B12 is 2 µg/day. In the preferred embodiment the dietary supplement contains 100 µg/day vitamin B12.

The preferred dietary supplement comprises vitamin C. Most of the functions of vitamin C are directly applicable to the health of connective tissue and their response to injury. Vitamin C, however tends to change the valence of copper, rendering copper unavailable to the body. It is good nutritional practice to dose extra copper when using mega doses of vitamin C. The RDA for vitamin C is 50-60 mg/day. In the preferred embodiment the dietary supplement contains 500 mg/day vitamin C.

The preferred dietary supplement comprises magnesium. Magnesium is widely distributed in food. However, the refining and processing of foods tends to remove large amounts of magnesium. Magnesium fulfills so many essential functions that it is almost impossible to single out any one function as most critical. There is no established RDA for magnesium because it is ubiquitous in nature. Nonetheless, the food and nutrition board of the national academy of sciences has recommended intake based on age and gender of 40-400 mg/day as safe and adequate. In the preferred embodiment the dietary supplement contains 400 mg/day magnesium in the form of magnesium citrate.

The preferred dietary supplement comprises vitamin E. Vitamin E is synthesized only by plants, and therefore is found primarily in plant products, particularly in plant oils. Vitamin E affects almost every aspect of health to some degree in its role and function as a scavenger of free radicals. The RDA for vitamin E is 8-10 mg/day. In the preferred embodiment the dietary supplement contains 400 mg/day vitamin E.

The preferred dietary supplement comprises vitamin D3. Vitamin D3 is important in calcium, phosphate and magnesium absorption. Excess vitamin D causes hypercalcemia. Clinical signs are weakness, nausea, headaches, abdominal pain, cramps and diarrhea. Intake of vitamin D is not absolutely essential if adequate skin exposure to sunlight is available. The RDA for vitamin D3 is 400 IU/day. However, recent research has shown that the recommended dose of vitamin D3 should be 1000-2000 IU/day due to the newly discovered multiplicity of critical functions in metabolism other than simply bone health. In the preferred embodiment the dietary supplement contains 1000 IU/day vitamin D3.

The preferred dietary supplement comprises zinc. Zinc, in addition to cell growth and replication, has specific roles in sexual maturation, fertility, reproduction, night vision, immune function, taste and appetite. Zinc, with copper as a stabilizing influence, is vital to genetic stability and expression during cellular replication. Deficiencies or excesses of zinc can result in mutated cellular replication leading to disease states. Thus, zinc should be supplemented in balance with copper to protect the cellular reproductive function. The RDA for zinc is 12-15 mg/day. In the preferred embodiment the dietary supplement contains 25 mg/day of zinc in the form of zinc citrate.

The preferred dietary supplement comprises manganese. Manganese plays unique and vital roles in the synthesis of macromolecular components of connective tissues, especially for bone and cartilage. Since acute, severe deficiencies of manganese are rare, defects of manganese status appear to occur in active individuals during periods of stress, or from a life-long, chronic, intermittent, or marginal deficiency. Acute deficiency symptoms are not usually encountered but rather, as with copper and zinc, chronic or marginal deficiencies in manganese uptake results in decreased synthesis of connective tissues leading to loss of integrity for joints and bones. The RDA for manganese is 2.0 mg/day. In the preferred embodiment the dietary supplement contains 10 mg/day of manganese in the form of manganese gluconate.

The preferred dietary supplement comprises copper. Modest doses of copper as organic chelates are used to maintain physiologic levels of cuproenzymes important to connective tissue, particularly in the athletic or active individual. Copper has a long history of medicinal uses, including treatment of inflammatory conditions, osteoporosis, and arthritis. Copper functions primarily as a component of metalloenzymes with essential functions, and also activates other enzymes. There is no RDA for copper. Current research however, has established a beneficial, safe and adequate intake of 2-8 mg/day. In the preferred embodiment the dietary supplement contains 8 mg/day of copper in the form of copper gluconate.

The preferred dietary supplement comprises biotin. Biotin is important for energy production and fat metabolism. Biotin is rather widespread among foods and is synthesized by intestinal flora. Simple deficiencies of biotin in humans in the absence of other nutrient deficiencies are rare. However, those at risk for biotin deficiency include individuals on antibiotic therapy, alcoholics, pregnant and lactating women, surgical burn patients and the elderly. Relatively low levels of biotin have also been reported in physically active or athletic individuals. There is no RDA for biotin. However, the national academy of sciences food and nutrition board has published a nominal safe and adequate intake of 100-200 µg/day. In the preferred embodiment the dietary supplement contains 1000 µg/day of biotin.

The preferred dietary supplement comprises folate. Folate is important to blood cell formation as well as DNA and RNA synthesis. Deficiencies result in reduced cell division which is manifested as anemia, skin lesions and poor overall growth. Pregnant and lactating women, elderly persons and those taking certain folate antagonists such as aspirin, have an increased requirement for folate in the diet. The RDA for folate is 150-200 µg/day. In the preferred embodiment the dietary supplement contains 1000 µg/day of folate.

The preferred dietary supplement comprises chromium. Chromium is essential for optimal peripheral insulin action with respect to glucose intake. Studies of elderly and active adults with noninsulin-dependent diabetes mellitus showed improvement in glucose tolerance following a period of chromium supplementation. The RDA for chromium is 120 µg/day. In the preferred embodiment the dietary supplement contains 200 µg/day of chromium in the form of chromium polynicotinate.

The preferred dietary supplement comprises bioflavinoids. Bioflavinoids are a ubiquitous class of compounds found in plants. Most bioflavinoids exhibit antioxidant activity. Scavenging hydroxyl radicals, lipid peroxides, and reactive oxygen species has been repeatedly documented for many bioflavinoids. Bioflavinoids also reduce capillary fragility and/or permeability. This effect "spares" vitamin C, and is likely due to flavinoid chelation and antioxidant properties, particularly important to the physically active or elderly individual. Bioflavinoids appear to render other nutrients more effective as anti-inflammatory agents, especially vitamin C and proteolytic enzymes. There is no RDA for bioflavinoids. In the preferred embodiment the dietary supplement contains 1000 mg/day of bioflavinoids in the form of citrus bioflavinoids.

The preferred dietary supplement comprises glucosamine. Glucosamine is a naturally occurring amino sugar found in glycoproteins and glycosaminoglycans. Increased availability of glucosamine through supplements accelerates or enhances synthesis of hyaluronan, glycosaminoglycans and proteolysis There is no RDA for glucosamine. In the preferred embodiment the dietary supplement contains 1000 mg/day of glucosamine in the form of glucosamine sulfate.

The preferred dietary supplement comprises boron. Maintenance of boron intake by dietary manipulation and/or supplementation is recommended for bone loss conditions such as osteoporosis, fracture healing, arthritis and other degenerative joint diseases. There is no RDA for boron, however research has indicated that a boron intake of 3-6 mg/day is beneficial, safe and adequate. In the preferred embodiment the dietary supplement contains 3 mg/day of boron in the form of boron citrate.

In one embodiment, the dietary supplement is taken with an additional calcium supplement. Calcium should be given as a single dose, once per day in the evening. Calcium requirements should be provided by dietary means first. When increasing calcium intake through supplemental means to reach the recommended levels of 800-1200 mg/day, doses of 900 mg elemental calcium should be taken once daily with the evening meal. Supplementing calcium in the evening is preferred because calcium metabolizes differently in the early evening and is better absorbed at that time.

The present invention will be further illustrated by the following examples that are not limited.

EXAMPLES

A suitable *Aspergillus oryzae* protease preparation made with potato dextrin as the carbohydrate source is Protease A-DS, obtained from Amano Enzyme U.S.A. Co., Ltd., Elgin, Ill. This enzyme preparation contains not less than 300,000 HUT/gram. The protease extract can be given dissolved or suspended in water or in capsular form.

The dietary supplement employed in the following examples is comprised of the following vitamins in the indicated amounts:

| VITAMIN/MINERAL | AMOUNT PER SERVING (serving size 9 capsules) |
|---|---|
| Vitamin A (as retinyl palmitate) | 5,000 IU |
| Vitamin B1 (as thiamin mononitrate) | 100 mg |
| Vitamin B2 (as riboflavin) | 50 mg |
| Vitamin B3 (as niaciniaminde) | 300 mg |
| Vitamin B5 (as pantothenic acid) | 1,000 mg |
| Vitamin B6 (as pyridoxine hydrochloride) | 50 mg |
| Vitamin B12 (as cyanocobalamin) | 100 mcg |
| Vitamin C (as ascorbic acid) | 500 mg |
| Magnesium citrate | 400 mg |
| Vitamin E (as d-alpha-tocopherol) | 400 IU |
| Vitamin D3 (as cholecalciferol) | 1000 IU |
| Zinc Citrate | 25 mg |
| Manganese Gluconate | 10 mg |
| Copper Gluconate | 8 mg |
| Biotin (as d-biotin FCC) | 1 mg |
| Folate (as folic acid) | 1 mg |
| Chromium polynicotinate | 200 mcg |
| Citrus bioflavinoids | 1,000 mg |
| Glucosamine Sulfate (13.2% potassium) | 1,000 mg |
| Boron Citrate | 3 mg |

Example 1

A 55-year-old female was admitted to the hospital for emergency bowel/appendix surgery. Three days later she underwent surgery to excise a short segment of bowel including two sites of abscess. Postoperatively, she had a prolonged course of bowel recovery. On post operative day 10, she continued to exhibit abdominal distension and nausea. She remained on clear liquids and it was suggested by the surgeon that a port be inserted into her upper chest for ease of treatment with fluids and antibiotics. On post operative day 11 in lieu of the port placement, the patient was placed on the enzyme therapy regimen of the present invention. The patient was immediately dosed with six grams (2,400,000 HUT) of the Aspergillus oryzae protease preparation described herein dissolved in water. This dose was repeated 3 more times throughout the day for a total daily dose of 9,600,000 HUT. At the end of post operative day 11, radiological reports illustrated that small bowel dilation may have been slightly less than was seen on the previous study. On post operative day 12, the patient again received 4 doses of 6 grams (2,400,000 HUT) of the *Aspergillus oryzae* protease preparation described herein dissolved in water for a total daily dose of 9,600,000 HUT. The scan taken on post operative day 12 illustrated that air was in the transverse and descending colons but not definitely seen in the rectum. The scan taken at post operative day 13, after the second full day of treatment illustrated that the dilation of small bowel loops had decreased and air was now observed in the region of the rectum in addition to the transverse and descending colons. According to the radiologist, these findings were consistent with a resolving partial small bowel (inflammatory) obstruction. The next morning, on post operative day 14, after 3 full days of treatment, the symptoms had resolved sufficiently as to allow the patient to be discharged.

Example 2

A 60-year-old female with relapsing-remitting multiple sclerosis (MS) began taking the protease preparation of the invention following a MS relapse involving numbness and weakness of her legs and hands. The patient received six grams of the claimed *Aspergillus oryzae* protease preparation dissolved in water on an empty stomach four times daily for a total daily dose of approximately 9,600,000 HUT. Concurrently, the patient received three nutritional supplement capsules three times daily given with food and two calcium capsules given once per day with the evening meal. The patient regained the strength and feeling she lost in her right leg. In addition, an unexplained stiffness and pain in her right hand also improved.

Example 3

A 79-year-old male sustained a back injury and was advised by doctors that the physical trauma of the injury would take approximately six months to heal. The patient, in hopes of a shortened healing time, began taking the *Aspergillus oryzae* protease preparation and nutritional supplement regimen of the present invention. The patient received six grams of *Aspergillus oryzae* protease preparation of the present invention dissolved in water four times daily on an empty stomach, for a total daily dose of approximately 9,600,000 HUT. Concurrently, the patient received three nutritional supplement capsules three times daily given with food. Within 1 month of beginning the protocol described herein, the patient was pain free and regained both flexibility and range of motion.

Example 4

An 84-year-old woman diagnosed as having severe Alzheimer's disease was unable to communicate with her family, was confined to a chair and necessitated the use of diapers. The patient was placed on the protease and dietary supplement protocol of the present invention. She received six grams of the claimed *Aspergillus oryzae* protease preparation dissolved in water four times daily on an empty stomach, for a total daily dose of approximately 9,600,000 HUT. Concurrently, the patient received three nutritional supplement capsules three times daily given with food. Within two weeks, the patient was able to walk, participate in conversations and recognized family members.

Example 5

A 54-year-old female patient was diagnosed with chronic obstructive pulmonary disease (COPD) based on a chest X-Ray, breathing test and physical exam by a pulmonologist. The patient was placed on a tiotropim bromide inhaler and a levalbuterol inhaler. In addition to these therapies, the patient also began taking six grams of the *Aspergillus oryzae* protease preparation of the present invention dissolved in water four times daily on an empty stomach, for a total daily dose of approximately 9,600,000 HUT. Concurrently, the patient received three nutritional supplement capsules three times daily given with food and two calcium capsules given once per day with the evening meal. After one week, her fatigue was drastically decreased and energy and concentration markedly increased. Approximately 1 month later, the patient increased her nutritional supplement dose to 4 capsules three times daily. Within days of increasing the dose, the patients energy and concentration further improved to the point where day-time naps were no longer necessary.

Example 6

A 55 year-old-female patient was diagnosed with osteopenia, a reduction in bone tissue and density. The patient was placed on the protease and dietary supplement protocol of the present invention. She received six grams of the claimed *Aspergillus oryzae* protease preparation dissolved in water four times daily on an empty stomach, for a total daily dose of approximately 9,600,000 HUT. Concurrently, the patient received three nutritional supplement capsules three times daily given with food and two calcium capsules given once per day with the evening meal. Since beginning the protease and nutritional supplement protocol claimed herein, the patient has exhibited complete reversal of bone and tissue loss associated with bone density loss.

Example 7

A 57 year-old-female patient was diagnosed with a subretinal hemorrhage. The patient was placed on the protease protocol of the present invention. She received six grams of the claimed *Aspergillus oryzae* protease preparation dissolved in water once daily on an empty stomach, for a total daily dose of approximately 2,400,000 HUT. Concurrently, the patient received three nutritional supplement capsules three times daily given with food and two calcium capsules given once per day with the evening meal. One week after beginning the protocol, an improvement of 25% was noted. Sixty days after onset of treatment, an improvement of 90% was noted.

Example 8

A 64 year-old-male patient accidentally scalded his left hand with boiling water leading to blistering, edema, inflammation and swelling along with severe pain. After placing the scalded hand under cold water for approximately 14 minutes, the patient took 1,000 mg of Paracetamol tablets. The wound was bandaged with a Urgutol dressing. The patient then received six grams of the claimed *Aspergillus oryzae* protease preparation dissolved in water, on an empty stomach. Within 30 minutes, the severe pain was eliminated and within 30 minutes the swelling and inflammation had been considerably reduced. Approximately 7 hours after receiving the first dose of the claimed Aspergillus oryzae protease preparation, the patient was administered a second dose of 6 grams of the claimed preparation dissolved in water, for a total daily dose of 4,800,000 HUT. Within 35 minutes of receiving the second dose, the discomfort was completely eradicated and the areas of inflammation were noticeably disappearing. Two days later, when the dressings were removed, the hand appeared to be completely normal, with virtually no signs of the accident.

Example 9

A 3-year-old thoroughbred fully was treated with the *Aspergillus oryzae* protease preparation of the present invention after suffering with tying up syndrome. The horse received a single dose of the enzyme preparation claimed herein at a dose of 27 grams, 10,800,000 HUT, dissolved in water on an empty stomach. Within minutes the horse exhibited relaxed muscularity and walked out of the severe cramping discomfort.

Example 10

A mare suffering from a hematoma was administered the protease preparation of the present invention. The *Aspergillus oryzae* protease preparation was administered at a dose of 27 grams four times daily on an empty stomach for a total daily dose of 43,200,000 HUT per day. No other treatment was used in this case. Within four days of treatment the hematoma was no longer detectable.

Example 11

An adult male horse was diagnosed with a severely injured coffin joint in his right forelimb. According to the horse's veterinarian, there was no chance for recovery and it was suggested that the horse be euthanized. The horse went from lame to crippled to being forced to lay down only standing to urinate and sometimes eat. It was at this time that the horse was placed on the *Aspergillus oryzae* protease preparation of the present invention. The horse received 27 grams of *Aspergillus oryzae* protease preparation four times daily on an empty stomach for a total daily dose of approximately 43,200,000 HUT per day. In addition, the horse received the equivalent of 45 capsules of the nutritional supplement in powder form twice daily with feedings. Within six weeks he began standing for a significantly longer period of time putting all of his weight on his two back legs. Two months later, he began supporting himself on three limbs. Six weeks following that, he began slowly adding weight back to his injured right forelimb. Five months after beginning the protocol the grating and popping sound of bone on bone contact was almost totally gone. The horse soon regained the ability to walk on all four legs.

Example 12

An 8-year-old Jack Russell terrier was diagnosed with Lyme's Disease. Upon examination the dog was found to be suffering badly from renal failure. The veterinarian gave the dog a very poor prognosis stating that she had never seen a dog doing as badly as this dog recover from renal failure. The dog began receiving three grams of *Aspergillus oryzae* protease preparation of the present invention on an empty stomach three times daily (3,600,000 HUT). In addition, the dog received two nutritional capsules twice daily with meals. Within two months the dog made a complete recovery and was back to digging and hunting as she was before the illness.

Example 13

A 9-year-old Welsh Corgi was diagnosed with chondrosarcoma in his right nasal cavity. The veterinarians gave the dog between one week and one month to live. The dog also received pain relieving medications from the veterinarian. Soon after this, the dog began treatment with the protease and nutritional supplement protocol of the present invention. He received three grams of *Aspergillus oryzae* protease dissolved in water on an empty stomach four times daily for a total daily dose of approximately 4,800,000 HUT per day. In addition, the dog also received three nutritional capsules three times daily with meals. After only a few of days of taking the enzyme and nutritional supplement protocol the dog markedly improved so that he was taken off the pain relieving medication. After three-four weeks the dog was breathing through his nostrils freely again and regained both energy and appetite. After six months the enzyme dose was discontinued and reinstituted as a maintenance dose of 3 grams three times daily. One year later the dog exhibited no evidence of chondrosarcoma.

Example 14

A 7-year-old female Rottweiler was diagnosed with osteosarcoma. According to the veterinarian unless limb salvage procedures were to be undertaken, the most rapid and potentially curable option was partial or total limb amputation. The elective surgery was declined and the dog was placed on the enzyme protocol of the present invention. The dog received six grams of the *Aspergillus oryzae* protease preparation dissolved in water or in capsule form on an empty stomach four times daily, for a total daily dose of approximately 9,600,000 HUT per day. In addition, the dog received three nutritional supplement capsules three times daily with food. On day 50 after beginning the enzyme protocol a small fluid filled mass was found. On day 56 the small mass was drained. On day 63 post enzyme treatment, the dog was taken to another veterinarian. This veterinarian noticed that the primary tumor had become soft and ulcerated. A second mass was found to be totally necrotic. The dog was maintained on the enzyme protocol and was given Baytril for possible infection associated with the large amount of necrotic tissue sloughing-off from the tumor mass. On day 65 post enzyme treatment the dog was taken to the emergency room for massive bleeding from the tumor which could not be stopped after routine bandage change. The dog was given a sedative to lower blood pressure. The necrotic tissue was removed and the area was packed with sterile gauze and the pressure bandage was replaced. Surgery was scheduled for day 68 after the commencement of enzyme therapy. Surgery was performed to remove additional necrotic tissue. At this time laser surgery was also performed to cauterize the main feeder vein to the primary tumor in hopes of controlling the bleeding. During the surgery, the surgeon found that the second mass has also become totally necrotic as well as the surrounding tissue. The second mass was removed. The primary tumor was found to be full of pus and serous fluid.

Example 15

A 13-year-old Black Labrador Retriever developed a mass on his limb. Upon noticing the mass, the dog began treatment with the protease protocol of the present invention. He received six grams of *Aspergillus oryzae* protease dissolved in water on an empty stomach four times daily for a total daily dose of 9,600,000 HUT per day. After 4 weeks of treatment, the dog was scheduled for surgery to remove the mass. Upon removal of the mass, the, the pathologist that removed the mass noted that the tumor was >90% necrotic.

What is claimed is:
1. A method of treating an inflammatory disease in a mammal in need thereof, comprising orally administering to said mammal a composition comprising an *Aspergillus oryzae* protease preparation, in an amount greater than about 2,000,000 HUT per day, wherein said protease preparation is protease A-DS produced by *Aspergillus oryzae* using potato dextrin as the carbohydrate source.

2. The method according to claim 1, wherein said composition is given on an empty stomach.

3. The method according to claim 1, wherein said composition is given 4 times per day.

4. The method according to claim 1, wherein said inflammatory disease is selected from the group consisting of rheumatoid arthritis, multiple sclerosis, Crohn's disease, viral infection, soft tissue injury, bacterial infection, solid tumor malignancy, osteoporosis, osteopenia, chronic obstructive pulmonary disease, and Alzheimer's disease.

5. A method of treating inflammatory disease in a mammal in need thereof, comprising orally administering to said mammal composition comprising an *Aspergillus oryzae* protease preparation, in an amount greater than about 2,000,000 HUT (or equivalent biological activity) per day, and a dietary supplement of vitamins and minerals and wherein said protease preparation is protease A-DS produced by *Aspergillus oryzae* using potato dextrin as the carbohydrate source.

6. The method according to claim 5, wherein said dietary supplement contains vitamin A, vitamin B1, vitamin B2, vitamin B5, vitamin B6, vitamin B12, vitamin C, magnesium citrate, vitamin E, vitamin D3, zinc citrate, manganese gluconate, copper gluconate, biotin, folate, chromium polynicotinate, citrus bioflavinoids, glucosamine sulfate, and boron sulfate.

7. The method according to claim 5, wherein said dietary supplement is given 2-3 times per day.

8. The method according to claim 5, wherein said dietary supplement is given with food.

9. The method according to claim 5, wherein said composition is given on an empty stomach.

10. The method according to claim 5, wherein said composition is given 4 times per day.

11. The method according to claim 5, wherein said inflammatory disease is selected from the group consisting of rheumatoid arthritis, multiple sclerosis, Crohn's disease, viral infection, soft tissue injury, bacterial infection, solid tumor malignancy, osteoporosis, osteopenia, chronic obstructive pulmonary disease, and Alzheimer's disease.

12. The method of claim 5, wherein said mammal is human.

13. The method of claim 12, wherein an additional dietary supplement of calcium is administered to said human.

14. The method of claim 13, wherein said calcium supplement is administered to said human at a dose of 900 mg/day.

15. The method of claim 13, wherein said calcium is administered to said human once daily.

16. The method of claim 15, wherein said once daily dose of calcium is administered to said human in the evening.

17. The method of claim 1, wherein the protease preparation is administered in an amount of about 4,800,000 HUT per day.

18. The method of claim 1, wherein the protease preparation is administered in an amount of about 9,600,000 HUT per day.

19. The method of claim 1, wherein the composition is administered to a dog or a horse.

* * * * *